United States Patent [19]

Ascione et al.

[11] Patent Number: 5,658,555

[45] Date of Patent: Aug. 19, 1997

[54] PHOTOPROTECTIVE/COSMETIC COMPOSITIONS COMPRISING SYNERGISTIC ADMIXTURE OF SUNSCREEN COMPOUNDS/ NANOPIGMENTS

[75] Inventors: Jean-Marc Ascione, Paris; Delphine Allard, Colombes, both of France

[73] Assignee: Société L'Oréal S.A., Paris, France

[21] Appl. No.: 463,304

[22] Filed: Jun. 5, 1995

[30] Foreign Application Priority Data

Jun. 3, 1994 [FR] France .................................. 94 06832

[51] Int. Cl.$^6$ ................................ A61K 7/42; A61K 7/40
[52] U.S. Cl. ................................ 424/59; 424/60; 424/401; 514/844; 514/938
[58] Field of Search ................................ 424/59, 60, 401

[56] References Cited

U.S. PATENT DOCUMENTS 5,302,376  4/1994  Forestier et al. ........................ 424/59

OTHER PUBLICATIONS

Shaath, N., "Encyclopedia of UV Absorbers for Sunscreen Products", Cosmetic & Toiletires, vol. 102, Mar. 1987 pp. 21–36.

Roelandts, R et al "A Survey of Ultraviolet Absorbers in Commercially Available Sun Products", International Journal of Dermatology, May 1983, vol. 22, pp. 247–255.

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting synergistically effective amount of (i) 2,4,6-tris [p-((2'-ethylhexyl)oxycarbonyl)anilino]-1,3,5-triazine and benzene-1,4-di(3-methylidene-10-camphorsulfonic)acid, optionally either partially or totally neutralized, together with photoprotecting synergistically effective amounts of (ii) particulates of at least one inorganic nanopigment which comprises a metal oxide, in a cosmetically acceptable vehicle, diluent or carrier therefor.

25 Claims, No Drawings

PHOTOPROTECTIVE/COSMETIC COMPOSITIONS COMPRISING SYNERGISTIC ADMIXTURE OF SUNSCREEN COMPOUNDS/ NANOPIGMENTS

CROSS-REFERENCE TO COMPANION APPLICATIONS

Copending applications [Attorney Docket No. 016800-028], Ser. No. 08/463,221, [Attorney Docket No. 016800-029], Ser. No. 08/463,505, [Attorney Docket No. 016800-030], Ser. No. 08/463,503, U.S. Pat. No. 5,489,431, [Attorney Docket No. 016800-031], Ser. No. 08/463,762, [Attorney Docket No. 016800-033], Ser. No. 08/463,508, [Attorney Docket No. 016800-034], Ser. No. 08/461,015, [Attorney Docket No. 016800-035], Ser. No. 08/463,507, [Attorney Docket No. 016800-036], Ser. No. 08/464,940, each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, typically an oil-in-water emulsion, combinatory immixture of (i) at least two particular and unique sunscreen compounds, namely, on the one hand, 2,4,6-tris[p-((2'-ethylhexyl)oxycarbonyl)anilino]-1,3,5-triazine and, on the other, benzene-1,4-di(3-methylidene-10-camphorsulfonic)acid, and (ii), as photoprotective agents that function by physically blocking radiation (UV diffusers and/or reflectors), inorganic nanopigments based on metal oxides, in particular on titanium dioxide. This admixture imparts enhanced solar protection factors to the subject compositions via an unexpected synergistic effect.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or I/V-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

Thus, EP-A-0,457,687 describes a particularly advantageous photoprotective/sunscreen combination comprising immixture of a hydrophilic UV-A screening compound, namely, benzene-1,4-di(3-methylidene-10-camphorsulfonic)acid, and a lipophilic UV-B screening compound, namely, 2,4,6-tris[p-((2'-ethylhexyl)oxycarbonyl)anilino]1,3,5-triazine. This admixture presents the principal advantages of providing nontoxic sunscreen compositions which, on the one hand, via a synergistic effect between the two screening compounds, exhibit high protection factors over a wide UV wavelength range (280–400 nm), which, on the other, are thermally and photochemically stable, and also which have good cosmetic properties. However, the sun protection factors on skin imparted by the subject compositions may, and particularly in respect of the so-called sensitive skin types and/or for skin continually exposed to the sun, still appear to be insufficient.

Therefore, need continues to exist in this art for even more efficacious photoprotective/cosmetic compositions.

SUMMARY OF THE INVENTION

It has now unexpectedly and surprisingly been determined that a unique combination of two particular sunscreen compounds, together with a nanopigment material, provides photoprotective/sunscreen compositions having protection factors which are markedly improved, and in all instances conspicuously superior to those which may be obtained, for an equal concentration of sunscreen compound or nanopigments and in a vehicle identical in nature, employing either of the sunscreen compounds or nanopigments alone.

Moreover, formulating said nanopigments into the photoprotective/sunscreen synergistic combination described above does not perturb or adversely affect the other desirable and advantageous properties thereof. Hence, improved cosmetically acceptable, nontoxic sunscreen compositions are hereby provided that accord broad (UV-A+ UV-B) and very high photoprotection, while incorporating limited concentrations of sunscreen compounds/agents.

Briefly, the present invention features novel photoprotective/cosmetic compositions comprising, in a cosmetically acceptable vehicle, diluent or carrier, (i) an effective amount of 2,4,6-tris[p-((2'-ethylhexyl)oxycarbonyl)anilino]-1,3,5-triazine, as a first sunscreen compound, and an effective amount of benzene-1,4-di(3-methylidene-10-camphorsulfonic)acid, optionally either partially or totally neutralized, as a second sunscreen compound, as well as (ii) an effective amount of inorganic nanopigments based on metal oxides, as yet a third sunscreen agent.

The present invention also features the use of such compositions as, or for the formulation of, sunscreen/ cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

DETAILED DESCRIPTION OF BEST MODE AND PREFERRED EMBODIMENTS OF THE INVENTION

More particularly according to the present invention, by the term "nanopigments" are intended pigments whose average primary particle size does not exceed 100 nm, and which preferably ranges from 5 nm to 100 nm, even more preferably from 10 to 50 nm.

The use of inorganic pigments based on the metal oxides, and in particular on titanium dioxide, is generally known to the art of solar protection. It too is known that these materials, whether or not in combination with conventional organic screening compounds absorbing UV-A and/or UV-B irradiation, impart to the sunscreen compositions comprised thereof a certain relatively limited inherent or additional photoprotective characteristic, by physically blocking the UV rays (reflection and/or diffusion). Nonetheless, the potentiating or synergistic properties of the particular pigments (nanopigments) of the present invention are particularly surprising in respect of unexpectedly enhancing the photoprotective power or capacity of the specific screening immixture of benzene-1,4-di(3-methylidene-10-camphorsulfonic)acid+2,4,6-tris[p-((2'-ethylhexyl)oxycarbonyl)anilino]-1,3,5-triazine. Moreover, as indicated in the examples given below, it will be appreciated that the use of pigments other than those according to the present invention (nanopigments) does not elicit any synergistic effect vis-a-vis the aforesaid immixture.

The 2,4,6-tris[p-((2'-ethylhexyl)oxycarbonyl)anilino]-1,3,5-triazine (compound A) according to this invention is a sunscreen compound that is per se known to this art and is active in the UV-B range, is a solid material and is marketed under the trademark "UVINUL T 150" by BASF. This compound has the following structural formula (I):

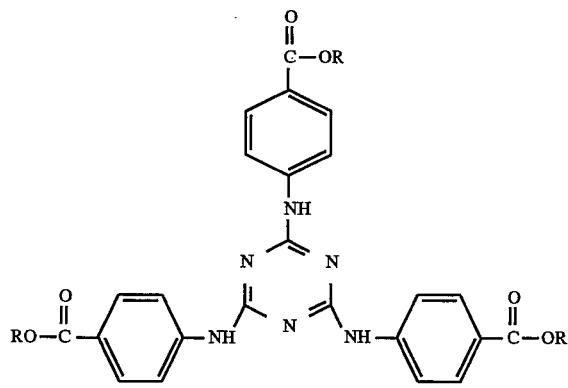

in which R is a 2-ethylhexyl radical.

Benzene-1,4-di(3-methylidene-10-camphorsulfonic)acid and the various salts thereof (compound B), which are described especially in FR-A-2,528,420 and FR-A-2,639,347, are also sunscreen compounds that are per se known to this art (so-called broad-band screening compounds) and which absorb ultraviolet rays of wavelengths ranging from 280 to 400 nm, with absorption maxima from 320 to 400 nm, in particular at about 345 nm. These screening compounds have the following structural formula (II):

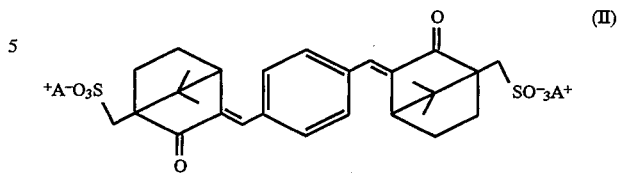

in which A is a hydrogen atom, an alkali metal or, alternatively, a radical $NH(R)_3^+$, wherein the radicals R, which may be identical or different, are each a hydrogen atom, a $C_1$–$C_4$ alkyl or hydroxyalkyl radical or, alternatively, a group $M^{n+}/n$, wherein $M^{n+}$ is a polyvalent metal cation in which n is equal to 2, 3 or 4, $M^{n+}$ preferably being a metal cation selected from among $Ca^{2+}$, $Zn^{2+}$, $Mg^{2+}$, $Ba^{2+}$, $Al^{3+}$ and $Zr^{4+}$. It should be appreciated that the above compounds of formula (I) may exist as "cis-trans" isomers about one or more double bond(s) and that all such isomers are within the scope of the present invention.

The compound A is advantageously present in the compositions according to the invention at a concentration ranging from 0.1% to 10% by weight, and preferably from 0.5% to 5% by weight, relative to the total weight of the composition, and compound B is advantageously present at a concentration ranging from 0.2% to 15% by weight, and preferably from 0.5% to 10% by weight, also relative to the total weight of the composition. The overall content of the mixture of compound A and compound B preferably does not exceed 15% of the total weight of the final composition.

The metal oxides constituting the nanopigments according to the present invention comprise those which are per se known for their photoprotective activity. Thus, they are advantageously selected from among titanium oxide, zinc oxide, iron oxide, zirconium oxide, cerium oxide, or mixtures thereof.

Such coated or uncoated metal oxide nanopigments are materials known to this art and described, in particular, in EP-A-0,518,773, hereby expressly incorporated by reference. Additional and commercially available nanopigments not described therein, but which are also suitable according to this invention include the products marketed under the trademarks UVT M 160, UVT M 212 and UVT M 262 by Kemira, and MT 100 SA and MT 100 SAS by Tayca.

As indicated above, the average primary particle size of the nanopigments present in the compositions of the invention generally ranges from 5 nm to 100 nm, preferably from 10 to 50 nm.

In a preferred embodiment of the invention, inorganic nanopigments are employed that are based on titanium dioxide. This titanium dioxide may be in a crystallized state of rutile and/or anatase type, and/or in an amorphous or substantially amorphous form. As indicated above, this pigment either may or may not then be coated, but it is preferable to use coated pigments, for example coated with alumina and/or aluminum stearate.

The nanopigments are typically present in the compositions according to the invention at a concentration ranging from 0.1% to 30% by weight, and preferably from 1% to 20% by weight, relative to the total weight of the composition.

From a practical standpoint, the aforesaid two compounds A and B and the nanopigments are preferably present in the final composition in the respective proportions such that the synergy is optimal, as regards the protection factor imparted by the resulting association. The exact range of the [screening compounds/nanopigments] weight ratios in which this optimal synergy is actually attained may vary slightly depending on the total amount of sunscreen agents used.

Moreover, the concentrations and ratios of compounds A and B and the nanopigments are typically selected such that the sun protection factor of the final composition is preferably at least 2.

In a preferred embodiment of the present invention, the cosmetically acceptable vehicle, diluent, carrier or support in which the various compounds A and B and the nanopigments are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, $\beta,\beta$-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, $\alpha$-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-$\alpha$-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, *J. Mol. Biol,* 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

A photoprotective/sunscreen formulation in accordance with the invention (Formulation 1) was prepared in the form of an emulsion of oil-in-water type containing (the amounts are expressed as % by weight relative to the total weight of the composition):

| | |
|---|---|
| (a) 2,4,6-Tris[p-((2'-ethylhexyl)oxycarbonyl)anilinol-1,3,5-triazine ("Uvinul T150") (first sunscreen) | 5% |
| (b) Benzene-1,4-di(3-methylidene-10-camphour- | 3% AM |

-continued

| | |
|---|---|
| sulfonic) acid (second sunscreen) | |
| (c) Nanopigments of TiO$_2$ ("MT 100 T" marketed by Tayca) (average primary particle size: 15 nm) | 5% |
| (d) Glyceryl monostearate/polyethylene glycol stearate mixture containing 100 moles of EO ("ARLACEL 165" marketed by ICI) | 2% |
| (e) Stearic acid | 2% |
| (f) Stearyl alcohol | 1% |
| (g) Petrolatum | 3% |
| (h) Polydimethylsiloxane ("SILBIONE OIL 70 047 V 300" marketed by Rhône-Poulenc) | 1% |
| (i) Neopentyl glycol diisooctanoate ("SALACOS 525" marketed by SACI) | 23% |
| (j) Glycerol | 5% |
| (k) Acrylic acid/ethyl acrylate crosslinked copolymer as a 28% aqueous dispersion ("ACRYSOL 33" marketed by Rohm & Haas) | 1% AM |
| (l) Triethanolamine | qs pH 7 |
| (m) Preservatives | qs |
| (n) Water | qs 100% |

Two comparative formulations were also prepared, having the same composition as that above except that the first comparative formulation (Formulation 2) was devoid of any sunscreen and contained only the TiO$_2$ nanopigments at a concentration of 5%, and the second comparative formulation (Formulation 3) was devoid of TiO$_2$ nanopigments and contained only the first and second sunscreens indicated above of 5% and 3%, respectively.

Each Of these emulsions was prepared by dissolving the first photoprotective/sunscreen agent in the fatty phase and then adding the emulsifying agents into this fatty phase, heated to about 80° C., and, lastly, adding with rapid stirring, the aqueous phase containing the second photoprotective/sunscreen agent, preheated to this same temperature.

For each of the formulations thus prepared, the sun protection factor (SPF) associated therewith was then determined. This factor was determined by using the in vitro method described by B. L. Diffey et al, in *J. Soc. Cosmet. Chem.*, 40, 127–133 (1989); this technique entailed determining the monochromatic protection factors every 5 nm over a range of wavelengths from 290 to 400 nm and in calculating therefrom the sun protection factor according to a given mathematical equation.

The results obtained, as a mean protection factor, are reported in Table I below:

TABLE I

| | FORMULATIONS | | |
|---|---|---|---|
| | 1 (Invention) | 2 (Comparative) | 3 (Comparative) |
| First sunscreen agent + second sunscreen agent (%) | 8 (5 + 3) | 0 | 8 (5 + 3) |
| Nanopigments (%) | 5 | 5 | 0 |
| Mean SPF | 27.4 | 4.0 | 12.3 |
| (standard deviation) | (3.6) | (0.2) | (2.4) |

These results clearly demonstrate the synergistic effect obtained with Formulation 1 in accordance with the invention, the sun protection factor attributed to this formulation being notably and significantly higher than the simple arithmetic sum of the sun protection factors associated with the two corresponding comparative formulations.

Also for purposes of comparison, three other formulations 1', 2' and 3' were moreover prepared, these being respectively identical to the above formulations 1, 2 and 3, with the sole difference being that the TiO$_2$ nanopigments were here replaced by a conventional TiO$_2$ pigment whose average particle size was on the order of 0.2. microns ("Hombitan anatase FF Pharma" marketed by Sachtleben), and the sun protection factors associated with these formulations were then examined as above. The results are reported in Table II below:

TABLE II

| | FORMULATIONS | | |
|---|---|---|---|
| | 1' (Comparative) | 2' (Comparative) | 3' (Comparative) |
| First sunscreen agent + second sunscreen agent (%) | 6 (5 + 3) | 0 | 8 (5 + 3) |
| Conventional pigments (%) | 5 | 5 | 0 |
| Mean SPF | 14.5 | 2.8 | 12.3 |
| (standard deviation) | (3.5) | (0.6) | (2.4) |

In contrast to the first test, these results do not demonstrate any synergistic effect.

EXAMPLE 2

Another specific example of a photoprotective/sunscreen composition in accordance with the invention, in the form of an emulsion of oil-in-water type, is as follows:

| | |
|---|---|
| (a) 2,4,6-Tris[p-((2'-ethylhexyl)oxycarbonyl)anilino]-1,3,5-triazine ("Uvinul T150") | 3 g |
| (b) Benzene-1,4-di(3-methylidene-10-camphorsulfonic) acid | 1.5 g |
| (c) Nanopigments of TiO$_2$ ("UVT-M262" marketed by Kemira) | 3 g |
| (d) 2-Ethylhexyl p-methoxycinnamate ("PARSOL MCX" marketed by Givaudan) (sunscreen) | 2 g |
| (e) Mixture of cetylstearyl alcohol and oxyethylenated cetylstearyl alcohol containing 33 moles of ethylene oxide ("SINNOWAX AO" marketed by Henkel) (emulsifying agent) | 7 g |
| (f) Mixture of glyceryl mono-, di- and tristearate (coemulsifying agent) | 2 g |
| (g) Diisopropyl adipate | 20 g |
| (h) Polydimethylsiloxane | 1.5 g |
| (i) Cetyl alcohol | 1.5 g |
| (j) Preservatives | qs |
| (k) Distilled water | qs 100 g |

This emulsion was prepared as in Example 1.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising photoprotecting synergistically effective amounts of (i) 2,4,6-tris[p-((2'-ethylhexyl)oxycarbonyl)anilino]-1,3,5-triazine and benzene-1,4-di(3-methylidene-10-camphorsulfonic)acid, optionally either partially or totally neutralized, together with photoprotecting synergistically effective amounts of (ii) particulates of at least one inorganic nanopigment which comprises a metal oxide, in a cosmetically acceptable vehicle, diluent or carrier therefor.

2. The sunscreen/cosmetic composition as defined by claim 1, comprising from 0.1% to 10% by weight of said triazine compound.

3. The sunscreen/cosmetic composition as defined by claim 2, comprising from 0.5% to 5% by weight of said triazine compound.

4. The sunscreen/cosmetic composition as defined by claim 2, comprising from 0.2% to 15% by weight of said sulfonic acid compound.

5. The sunscreen/cosmetic composition as defined by claim 3, comprising from 0.5% to 10% by weight of said sulfonic acid compound.

6. The sunscreen/cosmetic composition as defined by claim 1, said at least one inorganic nanopigment comprising titanium dioxide, zinc oxide, iron oxide, zirconium oxide, cerium oxide, or mixture thereof.

7. The sunscreen/cosmetic composition as defined by claim 6, said at least one inorganic nanopigment comprising coated or uncoated titanium dioxide.

8. The sunscreen/cosmetic composition as defined by claim 7, said at least one inorganic nanopigment comprising rutile, anatase or amorphous titanium dioxide.

9. The sunscreen/cosmetic composition as defined by claim 1, comprising from 0.1% to 30% by weight of said at least one inorganic nanopigment (ii).

10. The sunscreen/cosmetic composition as defined by claim 9, comprising from 1% to 20% by weight of said at least one inorganic nanopigment (ii).

11. The sunscreen/cosmetic composition as defined by claim 1, said sulfonic acid compound having the structural formula:

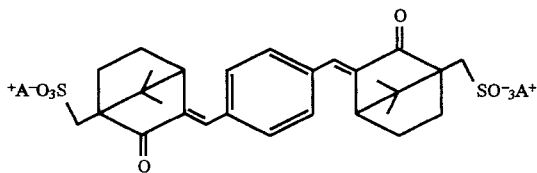

in which A is a hydrogen atom, an alkali metal or a radical $NH(R)_3^+$, wherein the radicals R, which may be identical or different, are each a hydrogen atom, a $C_1-C_4$ alkyl or hydroxyalkyl radical or a group $M^{n+}/n$, wherein $M^{n+}$ is a polyvalent metal cation in which n is equal to 2, 3 or 4.

12. The sunscreen/cosmetic composition as defined by claim 1, comprising an oil-in-water emulsion.

13. The sunscreen/cosmetic composition as defined by claim 1, comprising a water-in-oil emulsion.

14. The sunscreen/cosmetic composition as defined by claim 1, further comprising at least one additional hydrophilic or lipophilic organic UV-A and/or UV-B sunscreen.

15. The sunscreen/cosmetic composition as defined by claim 14, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

16. The sunscreen/cosmetic composition as defined by claim 1, further comprising at least one active agent for the artificial tanning and/or browning of human skin.

17. The sunscreen/cosmetic composition as defined by claim 1, further comprising at least one cosmetically acceptable adjuvant or additive.

18. The sunscreen/cosmetic composition as defined by claim 17, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

19. The sunscreen/cosmetic composition as defined by claim 1, comprising a nonionic vesicle dispersion, emulsion, cream, milk, gel, cream gel, ointment, suspension, dispersion, powder, solid stick, foam or spray.

20. The sunscreen/cosmetic composition as defined by claim 1, comprising a makeup.

21. The sunscreen/cosmetic composition as defined by claim 20, comprising an anhydrous or aqueous solid or paste, emulsion, suspension, or dispersion.

22. The sunscreen/cosmetic composition as defined by claim 1, comprising a shampoo, lotion, gel, emulsion, nonionic vesicle dispersion, hair lacquer, or rinse.

23. The sunscreen/cosmetic composition as defined by claim 1, having a sun protection factor of at least 2.

24. A method for protecting human skin and/or hair against the deleterious effects of ultraviolet irradiation, comprising topically applying thereto an effective amount of the sunscreen/cosmetic composition as defined by claim 1.

25. A method for protecting human skin and/or hair against the deleterious effects of solar radiation, comprising topically applying thereto an effective amount of the sunscreen/cosmetic composition as defined by claim 1.

* * * * *